United States Patent [19]

Ornstein et al.

[11] Patent Number: 5,045,472
[45] Date of Patent: Sep. 3, 1991

[54] REAGENT MIXTURE AND COMPOSITION FOR TREATING RED BLOOD CELLS TO EFFECT SPHERING

[75] Inventors: Leonard Ornstein, White Plains; Young R. Kim, Hartsdale, both of N.Y.

[73] Assignee: Technicon Instruments Corporation, Tarrytown, N.Y.

[21] Appl. No.: 537,887

[22] Filed: Jun. 14, 1990

Related U.S. Application Data

[60] Continuation of Ser. No. 425,506, Oct. 20, 1989, abandoned, which is a continuation of Ser. No. 158,124, Feb. 16, 1988, abandoned, which is a continuation of Ser. No. 802,956, Nov. 27, 1985, abandoned, which is a continuation of Ser. No. 510,824, Jul. 5, 1983, abandoned, which is a division of Ser. No. 277,539, Jun. 26, 1981, Pat. No. 4,412,004.

[51] Int. Cl.$^5$ .................. G01N 21/49; G01N 33/48; G01N 15/14
[52] U.S. Cl. ........................ 436/10; 436/17; 436/18; 436/63
[58] Field of Search .................... 436/8–18, 436/63; 252/408.1

[56] References Cited

U.S. PATENT DOCUMENTS

| | | | |
|---|---|---|---|
| 3,873,467 | 3/1975 | Hunt | 436/18 |
| 4,059,491 | 11/1977 | Iwasa et al. | 436/18 |
| 4,099,917 | 7/1978 | Kim | 436/10 |
| 4,102,810 | 7/1978 | Armstrong | 436/10 |
| 4,160,644 | 7/1979 | Ryan | 436/10 |
| 4,213,876 | 7/1980 | Crews et al. | 436/18 |
| 4,230,601 | 10/1980 | Hill | 436/18 |
| 4,250,051 | 2/1981 | Armstrong | 436/17 |
| 4,299,726 | 11/1981 | Crews et al. | 436/10 |
| 4,322,313 | 3/1982 | Raaijhakers | 436/10 |

OTHER PUBLICATIONS

Deuticke, Biochim. Biophys. Acta, 163, pp. 494–500 (1968).
Ponder, Hemolysis and Related Phenomena, Grung & Stratton, New York, pp. 10–49 (1948).
Davis et al., J. Med. Lab. Technol., 26, pp. 26–30 (1969).

Primary Examiner—David L. Lacey
Assistant Examiner—William K. Y. Chan
Attorney, Agent, or Firm—Morgan & Finnegan

[57] ABSTRACT

A composition is disclosed of blood serum sample preparation for improved, more accurate and precise, electrooptical method for measuring erythrocyte volumes, individually and as an average.

34 Claims, 1 Drawing Sheet

REAGENT MIXTURE AND COMPOSITION FOR TREATING RED BLOOD CELLS TO EFFECT SPHERING

CROSS-REFERENCE TO RELATED APPLICATION

This application is a continuation of application Ser. No. 425,506, now abandoned, which was a continuation of application Ser. No. 158,124, now abandoned, which was a continuation of application Ser. No. 802,956, now abandoned, which was a continuation of application Ser. No. 510,824, which was a division of application Ser. No. 277,539, now U.S. Pat. No. 4,412,004.

BACKGROUND OF THE INVENTION

This invention relates generally to a method for sphering or sphering and fixing whole blood erythrocytes without volume change for accurate and precise cell volume measurement. More particularly, the method employs a series of dilution steps whereby a protein, externally provided or endogenously supplied and a sphering agent are added in a protein/sphering agent weight ratio of from about 20:1 to about 70:1, based on total sample volume, and the concentration of detergent in the final sample is from about 2 mg./100 ml. to about 10 mg./100 ml.

Methods which utilize the measured amount of light scattered from individual red cells (erythrocytes) to determine the individual and mean volumes of red cells, suffer from two kinds of errors:

1. The native human red cell is a biconcave disc and the amount of light scattered within a particular solid angle varies with the orientation of the cell with respect to the incident light beam.
2. During handling, i.e. dilution and pumping, the shape of the cells can change depending in part on the time between the drawing of the blood and the time of measurement and in part on the composition of the diluted blood sample.

For a discussion of the above, see Hemolysis and Related Phenomena, Chapter II, pp 10–49 by Eric Ponder (1948) and Transformation and Restoration of Biconcave Shape of Human Erythrocytes Induced by Amphiphilic Agents and Changes of Ionic Environment, Biochemica Et. Biophy. Acta, Bernard Deuticke, pp 494–500 (1968).

SUMMARY OF THE INVENTION

The present invention eliminates both of these sources of error and permits vastly improved methods for determination of human red blood cell volumes. It is well known, see for example Ponder supra, that it is possible to sphere red blood cells in isotonic solution without changing their volumes. Since the light scattering from a perfectly sphered cell is invariant with orientation in a light beam, the first kind of error is eliminated. However, such preparations are notoriously unstable and red cell lysis occurs at various times after sphering, depending on the choice of sphering agent and the properties of the individual blood samples.

It has now been discovered that prolonged stability of the sphered state can be achieved by controlling the absolute concentration of the sphering agent (typically a material with detergent properties) and the weight ratio of sphering agent to protein, either added or endogenous at any desired dilution in isotonic solution. This helps to assure shape consistency during processing and minimizes the second kind of error.

The method of this invention can be carried out generally in two ways:

A. A blood sample is diluted, typically about 1/1000, in an isotonic solution containing sphering agent (detergent) and albumin at the required concentrations; or B. The blood sample is diluted with an amount of isotonic solution containing the sphering agent at a concentration which is just sufficient to cause sphering when the dilution provides the correct ratio of sphering agent to the endogenous serum albumin (plasma protein) from the blood sample itself. The resulting sample is then simultaneously and/or successively fixed and further diluted by adding an isotonic solution of a fixing agent to harden the sphered cells and make them completely insensitive to processes which could otherwise cause them to change their shape or size or lyse and lose their contained hemoglobin.

In accordance with this invention, there is claimed a method for treating mammalian red blood cells in a sample to provide a sample which can be effectively measured electrooptically for determination of red blood cell volumes which comprises combining an anticoagulated whole blood sample with an isotonic solution containing sphering agent, and diluting an aliquot of the resulting sample with an isotonic solution containing protein and sphering agent. The weight ratio in the final sample of protein/sphering agent is from about 20:1 to about 70:1, preferably about 50:1 and the concentration of sphering agent is from about 2 mg./100 ml. to about 10 mg./100 ml., preferably about 3 mg./100 ml.

Preferably, whole blood sample is prediluted with saline, as diluent, resulting in about a 50% by volume dilution of sample to reduce viscosity and therefore assure reduction of volumetric pumping errors which stem from variations in blood sample viscosities. The subsequent dilution steps result in a final dilution of sample of about 1:1000 by volume to produce a dilution such that the probability of more than one cell passing through the incident light beam of the electrooptical detector during the detector's measuring time window is very low.

The detergent used in this method is preferably an alkali metal salt of an alkyl sulfate, said alkyl group containing from 10 to 16 carbon atoms. Sodium lauryl sulfate is most preferred.

The protein used in this method is preferably serum albumin, which is added externally.

Another preferred method of this invention is similar to the above-described method except that in lieu of the protein/sphering agent dilution step, the aliquot sample is treated with a fixing agent solution, preferably an isotonic glutaraldehyde-containing saline solution. In this method, the protein required is endogenously provided in the sample as plasma protein.

In another preferred embodiment of this invention, there is claimed a reagent for sphering red blood cells in a sample comprising a protein-sphering agent mixture whereby the weight ratio of protein to sphering agent is from about 20:1 to about 70:1 and the total concentration of sphering agent in the composite sample is from about 2 mg./100 ml. to about 10 mg./100 ml.

DETAILED DESCRIPTION OF THE INVENTION

The present invention is directed to a method of sphering mammalian red blood cells in an anticoagulated whole blood sample. The method involves the employment of a protein and a sphering agent in a specified weight ratio and a certain final sphering agent concentration.

In the absence of protein, after addition of a sphering agent, the amount of free sphering agent in solution is dependent upon the concentration of red cells (see Ponder above). Therefore, with a reagent with fixed optimal sphering agent concentration for a normal blood count, the degree of sphering could be either incomplete, with a blood with high red cell count per unit volume of solution, or could lead to lysis with a very low red blood cell count. Proteins, such as serum albumins, bind sphering agent reversibly and can therefore be used to buffer the effective concentration of sphering agent in the optimal range, independent of red cell count.

The preferred concentration of sphering agent is that amount which is just sufficient to cause sphering when buffered with a protein such as albumin or plasma protein at any particular dilution of sample. The protein albumin can be provided in either of two ways: by outside addition or endogenously as plasma protein in the serum sample.

In a preferred embodiment of this invention, the method involves combining a prediluted blood sample with an isotonic sphering agent-saline solution and then treating an aliquot thereof with a protein-sphering agent saline solution.

Preferably, the predilution step is carried out by diluting the serum sample about 50% by volume with a suitable isotonic diluent such as a saline solution. The resulting prediluted sample is combined with an isotonic solution containing a sphering agent (sometimes referred to herein as detergent). A typical first dilution results in a 50:1 dilution of sample. A further dilution is effected by treating an aliquot of the above sample with a protein-sphering agent solution to provide a dilution of sample of about 1000:1. The resulting sample contains sphered and stabilized erythrocytes at a feasible concentration for light scattering measurement. When such light scattering measurement is conducted employing a flow cell cytometer, the individual cell volumes can be determined as well as the number of cells. The mean volume can therefore also be calculated.

A critical feature of this method involves the weight ratio of protein/sphering agent and the concentration of sphering agent. By regulating these parameters within certain limits, the sphering process is effectively accomplished and the analytical results highly probative.

It has been found that a weight ratio of protein/sphering agent in the herein disclosed method is preferably from about 20:1 to about 70:1, with a ratio of 50:1 most preferred. For the final concentration of sphering agent, a concentration of from about 2 mg./100 ml. to about 10 mg./100 ml. is highly suitable, with a concentration of 3 mg./100 ml. most preferred.

The protein, externally supplied, is preferably a serum albumin. Other employable proteins include bovine, human and egg albumin.

In a second method of this invention, the protein/sphering agent second dilution step is replaced by treatment with an isotonic fixing agent solution. In this system, the protein for the first dilution is provided in endogenous form in the serum sample as plasma protein. An isotonic solution of a sphering agent is added in a volume sufficient to bring the endogenous plasma protein/sphering agent ratio and also the concentration of sphering agent within the preferred ranges. The preferred fixing agent is glutaraldehyde, used in an amount to provide a final glutaraldehyde concentration of from 0.1% to 0.4% by weight. The isotonic fixing agent solution is suitably formulated with saline or a saline-sphering agent mixture.

Because glutaraldehyde fixes red cells very rapidly, optimal buffering of the sphering agent concentration beyond the fixing agent addition step is considered less critical. As soon as the red cell content has been fixed, it becomes completely noncritical.

The sphering agent employed in either method is suitably an alkali metal (sodium, potassium, lithium, cesium or rubidium) salt of an alkyl sulfate wherein said alkyl contains from 10 to 16 carbons. Alkali metal lauryl sulfates are preferred, and sodium lauryl sulfate most preferred. Other suitable sphering agents which may be employed in these methods include fatty acids, phospholipids, etc. It is to be noted that some nominal "sphering agents" such as crude egg lecithin (see Ponder above) actually contain a sphering agent as a minor impurity. For example, pure lecithin is not a sphering agent. It is to be understood that the weight concentrations discussed are of the active principle in any impure "sphering agent" and not the crude weight concentration.

Both methods can be effected either continuously as in an automated system or in a discontinuous or discrete manner.

DETAILED DESCRIPTION OF THE DRAWING

Figure 1:
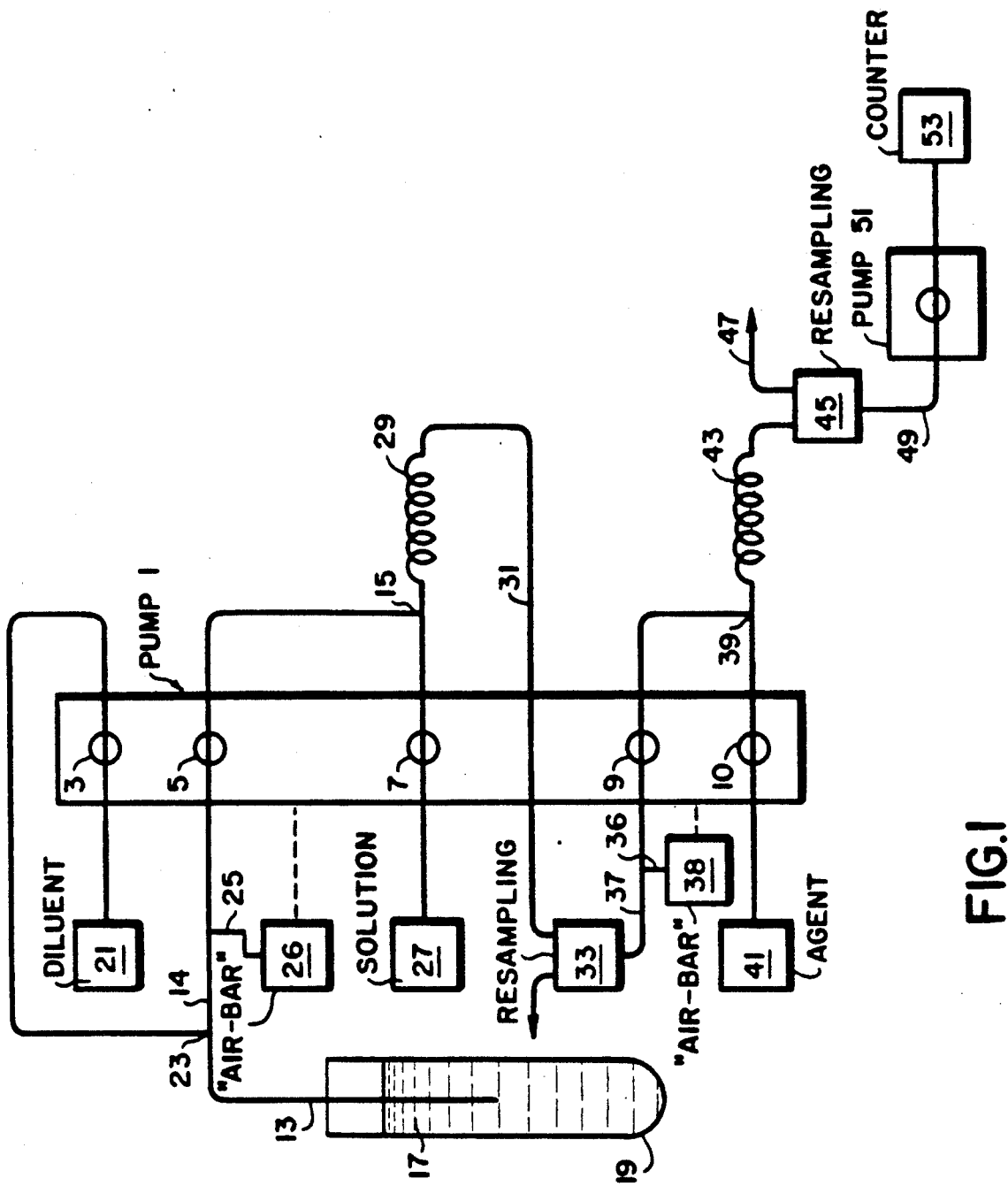
FIG. 1 represents a schematic flow sheet of the continuous system or apparatus according to one embodiment of the present invention for the treatment of a serum sample for eventual electrooptical measurement.

Referring to the sole figure, a system is illustrated for measuring the volume of individual red cells in a discrete anticoagulated blood sample treated in accordance with the present invention. However, it is within the contemplation of the present invention that the measurement of the volume of red cells in successive anticoagulated blood samples may be effected on a continuous basis, for example, as described in U.S. Pat. No. 3,740,143, assigned to a common assignee.

Such system comprises a peristaltic pump 1 including pump tubes 3, 5, 7, 9 and 10. As is understood, the relationship of the internal diameters of such pump tubes determines the proportioning of the sample and reactants introduced into the system. An aspirating probe 13 is connected along conduit 14, to the inlet of pump tube 5, whose outlet is connected to a junction 15. Probe 13 is adapted to be immersed into an anticoagulated blood sample 17 contained in a sample receptacle 19. It will be appreciated that probe 13 may be adapted, as described in U.S. Pat. No. 3,740,143, to be immersed, in turn, into successive sample receptacles, so as to effect the measurement of the red cell volumes of successive samples on a continuous basis.

Also, the inlet end of pump tube 3 is connected to a source 21 of appropriate diluent for effecting the first dilution of the sample 17. Upon operation of pump 1, diluent is passed along pump tube 3 to junction 23 in conduit 14, so as to be mixed with and dilute the sample being passed from the probe 13. Also, an air line 25 from an "air-bar" structure 26, as described in U.S. Pat. No. 3,306,229, assigned to a common assignee, whose operation is phased to that of the pump 1 as indicated by the dashed connector, operates periodically to introduce occluding air segments into conduit 14. The presence of such "intra-sample" air segments insures proper proportioning of the sample and reactants into the system (and effective wash between successive samples) as described in the referenced patent. Concurrently, an isotonic solution containing the sphering agent is passed from source 27 along pump tube 7 to junction 15, whereat it is mixed with the diluted sample passed along pump tube 5, to effect the second dilution of sample 17. The sample is flowed from junction 15 and through mixing coil 29, to effect a thorough mixing thereof, and subsequently along conduit 31 to a resampling fitting 33. Fitting 33 includes a waste outlet 35 and a resampling outlet 37 connected to the inlet of pump tube 9. The sample passes from outlet 37 and to junction 39 along pump tube 9, excess sample and "intra-sample" air segments introduced into fitting 33 being passed to waste along waste outlet 35. A second "air-bar" structure 38 reintroduces "intrasample" air segments along air line 36 into the diluted sample stream.

The inlet of pump tube 10 is connected to a source 41 of fixing agent. The outlet of pump tube 10 is connected to junction 39, whereat the fixing agent and the twice-diluted sample are mixed and passed to mixing coil 43, to insure mixing of the same. The outlet of mixed coil 43 is passed to a resampling fitting 45, which includes a waste outlet 47 and a resampling outlet 49, the latter being connected to the inlet of the single pump tube of a secondary peristaltic pump 51. The sample is passed from the outlet 49 and through pump 51 to a sheath-stream particle counter 53, of the type described in U.S. Pat. No. 3,740,143, supra. Again, excess sample and the "intra-sample" air segments are passed to waste along waste outlet 47. In counter 45, the red cells in the treated blood sample are confined to flow serially, so as to be individually counted and their volumes measured. The treated blood sample is thereafter passed to waste. The sphering of the red cells, according to the present invention, insures that the measured volume is independent of the orientation of the red cells as they progress through counter 53. In prior art, where the red cells were not properly sphered, the random orientation of the red cells proceeding through the particle counter often resulted in inaccurate volume determinations.

EXAMPLE I

A sample (0.37 ml.) of anticoagulated whole blood is prediluted with isotonic saline (0.23 ml.). An aliquot (0.16 ml.) of the resulting sample is combined with 4.2 ml. of an isotonic saline solution containing sodium lauryl sulfate (3 mg./100 ml.). An aliquot (0.16 ml.) of the resulting diluted sample is then treated with 4.0 ml. of an isotonic saline solution containing bovine serum albumin (0.1%) and sodium lauryl sulfate (3 mg./100 ml.). The final sample is placed in a flow cell and electrooptically measured. The red blood cell count and red blood cell volume were recorded.

EXAMPLE II

A sample (0.37 ml.) of anticoagulated whole blood is prediluted with isotonic saline (0.23 ml.). An aliquot (0.16 ml.) of the resulting sample is combined with 4.2 ml. of an isotonic saline solution containing sodium lauryl sulfate (3 mg./100 ml.). An aliquot (0.16 ml.) of the resulting diluted sample is then treated with 4.0 ml. of an isotonic saline solution containing glutaraldehyde (0.2%) and sodium lauryl sulfate (1 mg./100 ml.). The final sample is placed in a flow cell and electrooptically measured. The red blood cell count and red blood cell volume were recorded.

It should be understood by those skilled in the art that various modifications may be made in the present invention without departing from the spirit and scope thereof as described in the specification and defined in the appended claims.

What is claimed is:

1. A composition for use in a cytometer, comprising:
   (a) an anticoagulated whole blood sample aliquot, and
   (b) a reagent mixture consisting essentially of:
      (i) an isotonic aqueous solution;
      (ii) a sphering agent; and
      (iii) a protein, which reversibly binds said sphering agent;
   said protein and sphering agent being present in a weight ratio of protein to sphering agent from about 20:1 to about 70:1, and said sphering agent having a final concentration in the range of about 2 mg per 100 ml to about 10 mg per 100 ml in said reagent mixture.

2. The composition of claim 1, wherein said protein is a serum albumin.

3. The composition of claim 74, wherein said detergent is an alkali metal salt of an alkyl sulfate.

4. The composition of claim 3, wherein said alkali metal salt is an alkali metal lauryl sulfate.

5. The composition of claim 4, wherein said alkali metal laurel sulfate is sodium lauryl sulfate.

6. The composition of claim 74, wherein said detergent is an alkali metal salt of an alkyl sulfate, said alkyl containing from 10 to 16 carbon atoms.

7. The composition of claim 6, wherein said alkyl sulfate salt is an alkali metal lauryl sulfate.

8. The composition of claim 7, wherein said alkali metal lauryl sulfate is sodium lauryl sulfate.

9. The composition of claim 1, wherein the concentration of sphering agent is about 3 mg per 100 ml.

10. The composition of claim 1, wherein said protein and sphering agent are present in a weight ratio of protein to sphering agent of about 50:1.

11. The composition of claim 1, wherein said protein is selected from the group consisting of bovine serum albumin, human albumin, and egg albumin.

12. The composition of claim 1, wherein said protein is endogenous in a whole blood sample.

13. The composition of claim 1, wherein said sphering agent is a detergent.

14. The composition of claim 1, wherein said sphering agent is a phospholipid.

15. The composition of claim 1, wherein said sphering agent is a fatty acid.

16. The composition of claims 1, 13, 14, or 15, wherein said reagent mixture further includes a fixing agent.

17. The composition of claim 16, wherein said fixing agent is gluteraldehyde present in said reagent mixture in an amount providing a final gluteraldehyde concentration of from about 0.1% to 0.4% by weight.

18. A reagent mixture for sphering red blood cells in an anticoagulated whole blood sample, consisting essentially of:
- (i) an isotonic aqueous solution;
- (ii) a sphering agent;
- (iii) a protein, which reversibly binds said sphering agent;

said protein and sphering agent being present in said mixture in a weight ratio of protein to sphering agent from about 20:1 to about 70:1, and said sphering agent having a final concentration in the range of about 2 mg per 100 ml to about 10 mg per 100 ml in said reagent mixture.

19. The reagent mixture of claim 18, wherein said protein is a serum albumin.

20. The reagent mixture of claim 18, wherein said sphering agent is an alkali metal salt of an alkyl sulfate.

21. The reagent mixture of claim 20, wherein said alkyl sulfate salt is an alkali metal lauryl sulfate.

22. The reagent mixture of claim 21, wherein said alkali metal lauryl sulfate is sodium lauryl sulfate.

23. The regent mixture of claim 18, wherein said sphering agent is an alkali metal salt of an alkyl sulfate, said alkyl sulfate containing from 10 to 16 carbon atoms.

24. The reagent mixture of claim 23, wherein said alkyl sulfate salt is an alkali metal lauryl sulfate.

25. The reagent mixture of claim 24, wherein said alkali metal lauryl sulfate is sodium lauryl sulfate.

26. The reagent mixture of claim 18, wherein the concentration of sphering agent is about 3 mg per 100 ml.

27. The reagent mixture of claim 18, wherein said protein and sphering agent are present in a weight ratio of protein to sphering agent of about 50:1.

28. The reagent mixture of claim 18, wherein said protein is selected from the group consisting of bovine serum albumin, human albumin, and egg albumin.

29. The reagent mixture of claim 18 wherein said protein is endogenous in a whole blood sample.

30. The reagent mixture of claim 18, wherein said sphering agent is a detergent.

31. The reagent mixture of claim 18, wherein said sphering agent is a phospholipid.

32. The reagent mixture of claim 18, wherein said sphering agent is a fatty acid.

33. The reagent mixture of claims 18, 30, 31, or 32, further including a fixing agent.

34. The reagent mixture of claim 33, wherein said fixing agent is gluteraldehyde present in an amount providing a final gluteraldehyde concentration of from about 0.1% to 0.4% by weight.

* * * * *

UNITED STATES PATENT AND TRADEMARK OFFICE
CERTIFICATE OF CORRECTION

PATENT NO.    :    5,045,472

DATED         :    September 3, 1991

INVENTOR(S)   :    Leonard Ornstein and Young R. Kim

It is certified that error appears in the above-identified patent and that said Letters Patent is hereby corrected as shown below:

In Claim 3, Column 6, line 32, remove "74" and insert --13--.

In Claim 6, Column 6, line 38, remove "74" and insert --13--.

Signed and Sealed this

Thirteenth Day of December, 1994

Attest:

BRUCE LEHMAN

Attesting Officer                Commissioner of Patents and Trademarks